United States Patent
Nomura et al.

(10) Patent No.: US 10,485,703 B2
(45) Date of Patent: *Nov. 26, 2019

(54) LASER TREATMENT APPARATUS

(71) Applicant: KABUSHIKI KAISHA TOPCON, Itabashi-ku (JP)

(72) Inventors: Kazuhisa Nomura, Saitama (JP); Hideharu Suzuki, Nerima-ku (JP)

(73) Assignee: KABUSHIKI KAISHA TOPCON, Itabashi-ku (JP)

(*) Notice: Subject to any disclaimer, the term of this patent is extended or adjusted under 35 U.S.C. 154(b) by 1053 days.

This patent is subject to a terminal disclaimer.

(21) Appl. No.: 14/417,338

(22) PCT Filed: Aug. 9, 2013

(86) PCT No.: PCT/JP2013/071633
§ 371 (c)(1),
(2) Date: Jan. 26, 2015

(87) PCT Pub. No.: WO2014/041933
PCT Pub. Date: Mar. 20, 2014

(65) Prior Publication Data
US 2015/0173952 A1    Jun. 25, 2015

(30) Foreign Application Priority Data
Sep. 13, 2012 (JP) .................. 2012-202080

(51) Int. Cl.
*A61F 9/008* (2006.01)
*A61B 3/00* (2006.01)
*A61B 18/20* (2006.01)

(52) U.S. Cl.
CPC ........ *A61F 9/00823* (2013.01); *A61B 18/203* (2013.01); *A61F 9/008* (2013.01);
(Continued)

(58) Field of Classification Search
CPC combination set(s) only.
See application file for complete search history.

(56) References Cited

U.S. PATENT DOCUMENTS 5,943,118 A * 8/1999 Koschmieder ........ A61B 3/135
351/243
2003/0009155 A1   1/2003 Pawlowski et al.
(Continued)

FOREIGN PATENT DOCUMENTS

JP    2002 186640    7/2002
JP        4080174    4/2008
(Continued)

OTHER PUBLICATIONS

International Search Report dated Oct. 8, 2013 in PCT/JP13/071633 Filed Aug. 9, 2013.
(Continued)

*Primary Examiner* — Scott Luan
(74) *Attorney, Agent, or Firm* — Oblon, McClelland, Maier & Neustadt, L.L.P.

(57) ABSTRACT

Operations of a laser treatment apparatus are facilitated. A laser treatment apparatus of an embodiment includes an illumination system, observation system, irradiation system, illumination-area changing part, irradiation-condition setting part and controller. The illumination system illuminates an eye fundus. The observation system is used for observing the fundus illuminated. The irradiation system irradiates aiming light of a preset pattern and treatment light consisting of laser light of a pattern determined based on the preset pattern onto the fundus. The illumination-area changing part is used for changing an illumination area of the fundus by the illumination system. The irradiation-condition setting part sets irradiation condition of the aiming light and/or treatment light from the irradiation system. The controller controls the illumination-area changing part based on the set irradiation condition to change the illumination area.

6 Claims, 11 Drawing Sheets

(52) U.S. Cl.
CPC .......... *A61B 2018/2025* (2013.01); *A61B 2018/20359* (2017.05); *A61F 9/00821* (2013.01); *A61F 2009/00863* (2013.01); *A61F 2009/00897* (2013.01)

(56) References Cited

U.S. PATENT DOCUMENTS

| | | | |
|---|---|---|---|
| 2006/0100677 A1* | 5/2006 | Blumenkranz | A61F 9/008 607/89 |
| 2007/0129775 A1 | 6/2007 | Mordaunt et al. | |
| 2012/0050683 A1 | 3/2012 | Yates | |
| 2012/0150159 A1 | 6/2012 | Kunath-Fandrei et al. | |
| 2012/0165799 A1 | 6/2012 | Yamamoto | |

FOREIGN PATENT DOCUMENTS

| | | |
|---|---|---|
| JP | 2009 514564 | 4/2009 |
| JP | 4377405 | 12/2009 |
| JP | 2010 148635 | 7/2010 |
| JP | 2012 135550 | 7/2012 |
| WO | 2010 130456 | 11/2010 |

OTHER PUBLICATIONS

Office Action dated Mar. 16, 2018 in German Patent Application No. 11 2013 004 455.2 (with English language translation).

* cited by examiner

LASER TREATMENT APPARATUS

TECHNICAL FIELD

The present invention relates to a laser treatment apparatus used in ophthalmology.

BACKGROUND TECHNOLOGY

A laser treatment apparatus is used for photocoagulation treatment of retina etc. Laser treatment apparatuses configured to use aiming light of a preset pattern to take aim at a desire area of retina and then irradiate laser light onto treatment positions consisting of at least a part of this aiming pattern are known (see Patent Documents 1 and 2, for example).

PRIOR ART DOCUMENTS

Patent Documents

[Patent Document 1] Japanese Patent No. 4377405
[Patent Document 2] Japanese Unexamined Patent Application Publication No. 2009-514564

SUMMARY OF THE INVENTION

Problem that the Invention is to Solve

Regarding laser treatments using a laser treatment apparatus, it is necessary for an operator to carry out various kinds of operations such as hold of a contact lens contacting with an eye, adjustment of observation area, adjustment of irradiation positions of laser light, instruction of irradiation of laser light, etc. Performing such operations simultaneously is exceedingly difficult.

A purpose of the present invention is to facilitate operations of a laser treatment apparatus.

Means for Solving the Problem

A laser treatment apparatus of an embodiment includes: an illumination system that illuminates a fundus of an eye; an observation system for observing the fundus illuminated by the illumination system; an irradiation system that irradiates aiming light of a preset pattern and treatment light consisting of laser light of a pattern determined based on the preset pattern onto the fundus; an illumination-area changing part for changing an illumination area of the fundus by the illumination system; an irradiation-condition setting part that sets irradiation condition of the aiming light and/or treatment light from the irradiation system; and a controller that controls the illumination-area changing part based on the irradiation condition set by the irradiation-condition setting part to change the illumination area.

Effect of the Invention

According to the present invention, it is possible to facilitate operations of a laser treatment apparatus.

MODES FOR CARRYING OUT THE INVENTION

Examples of embodiments of a laser treatment apparatus according to the present invention will be described in detail referring to drawings. Technology described in the patent documents cited above may be applied to the following embodiments.

To begin with, directions are defined. A frontward direction is a direction from an optical system of an apparatus toward a patient and a backward direction is the opposite direction thereof. A crosswise direction (right-left direction) is a horizontal direction that is orthogonal to the front-back direction. A vertical direction is a direction orthogonal to both front-back and crosswise directions.

[Configuration]

Figure 1:
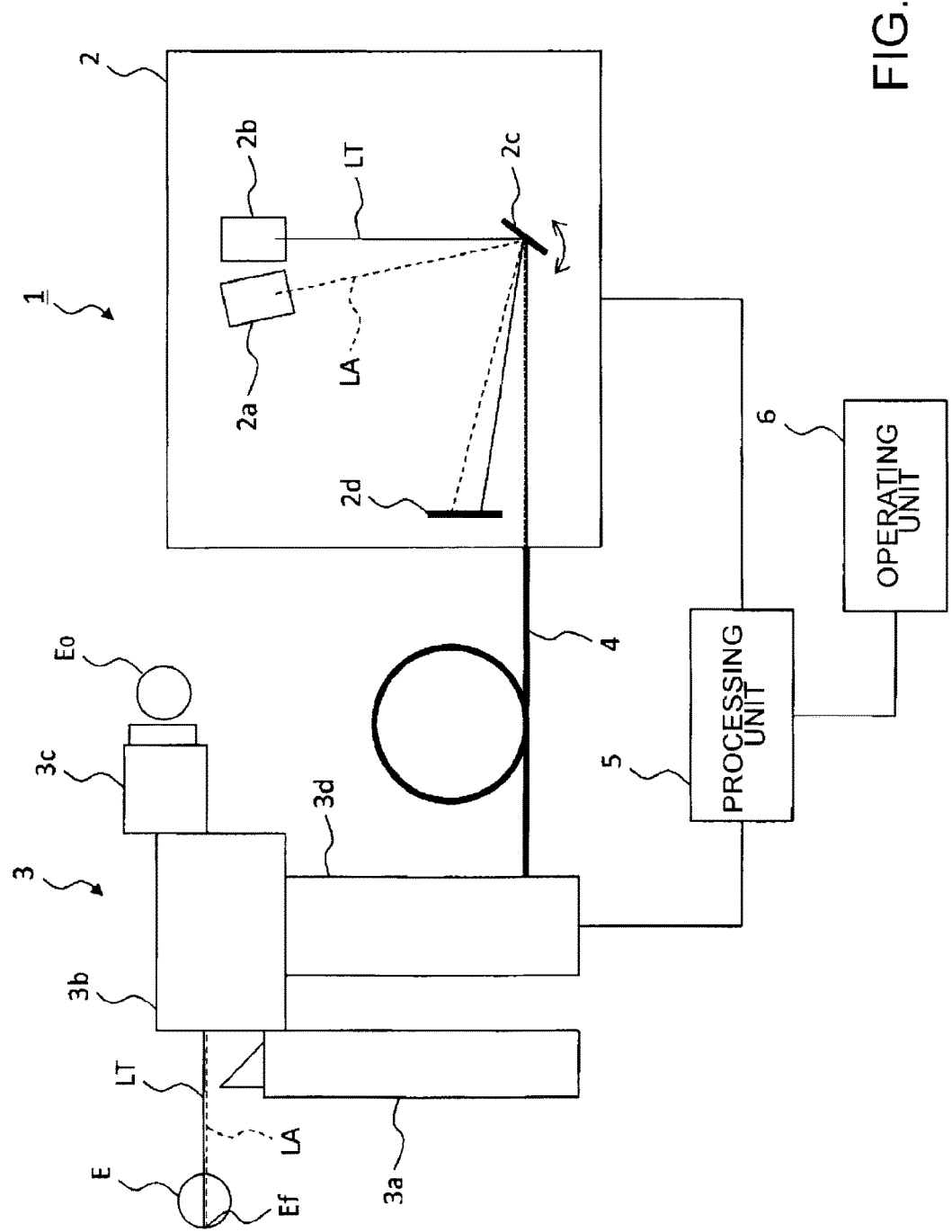
FIG. 1 is a schematic diagram illustrating a configuration example of a laser treatment apparatus according to an embodiment.

FIG. 1 illustrates a configuration example of a laser treatment apparatus 1 of the present embodiment. The laser treatment apparatus 1 is used for laser treatment of a fundus Ef of an eye E. The laser treatment apparatus 1 includes a light source unit 2, slit lamp microscope 3, optical fiber 4, processing unit 5 and operating unit 6. An operation microscope, indirect opthalmoscope, observation apparatus inserted in eyes, etc. may be used instead of the slit lamp microscope 3.

The light source unit 2 and slit lamp microscope 3 are optically connected via the optical fiber 4. The optical fiber 4 includes one or more optical waveguides. The light source unit 2 and processing unit 5 are connected such that signals may be transmitted. The slit lamp microscope 3 and processing unit 5 are connected such that signals may be transmitted. The operating unit 6 and processing unit 5 are connected such that signals may be transmitted. Methods of signal transmission may be wired or wireless.

The processing unit 5 may be a computer that operates by cooperation of hardware and software. Processing executed by the processing unit 5 is described later. The operating unit 6 includes various hardware keys and/or software keys (GUI). The hardware keys may be: buttons, handles, knobs provided in the slit lamp microscope 3; keyboard, pointing devices (mouse, trackball, etc.) provided in a computer (processing unit 5 etc.) connected to the slit lamp microscope 3; foot switches, operating panel, etc. provided separately from them, for example. The software keys may be displayed on a display device provided in the slit lamp microscope 3 or the computer described above, for example.

(Light Source Unit 2)

The light source unit 2 generates light to be irradiated onto the fundus Ef. The light source unit 2 includes an aiming light source 2a, treatment light source 2b, galvano mirror 2c and douser 2d. The light source unit 2 may be provided with any member other than the members shown in FIG. 1. For example, an optical element (lens etc.) entering light generated by the light source unit 2 into an end face of the optical fiber 4 may be provided in a location just before the optical fiber 4.

(Aiming Light Source 2a)

The aiming light source 2a generates aiming light LA for taking aim at a site to which laser treatment is performed. Arbitrary light source may be used as the aiming light source 2a. For example, in the case of applying a configuration that performs aiming while visually observing the fundus Ef, a light source emitting visible light recognizable by an operator's eye $E_O$ (laser light source, light emitting diode, etc.) is used as the aiming light source 2a. Alternatively, in the case of applying a configuration that performs aiming while observing a photographed image of the fundus Ef, a light source emitting light containing wavelength band sensible by an image sensor for acquiring the photographed image (laser light source, light emitting diode, etc.) is used as the aiming light source 2a. The aiming light LA is guided to the galvano mirror 2c. Action of the aiming light source 2a is controlled by the processing unit 5.

(Treatment Light Source 2b)

The treatment light source 2b emits laser light for treatment (treatment light LT). The treatment light LT may be visible or invisible laser light according to its usage. The treatment light source 2b may be a single laser light source emitting a plurality of laser light with different wavelengths or a plurality of laser light sources. The treatment light LT is guided to the galvano mirror 2c. Action of the treatment light source 2b is controlled by the processing unit 5.

(Galvano Mirror 2c)

The galvano mirror 2c includes a mirror with a reflecting surface, actuator that changes orientation of the mirror (direction of the reflecting surface). The aiming light LA and treatment light LT reach the same location on the reflecting surface of the galvano mirror 2c. The aiming light LA and treatment light LT are sometimes referred to as "irradiation light" collectively. Orientation of the galvano mirror 2c (direction of the reflecting surface) are changed at least to orientation for reflecting irradiation light toward the optical fiber 4 (orientation for irradiation) and orientation for reflecting irradiation light toward the douser 2d (orientation for stopping). Action of the galvano mirror 2c is controlled by the processing unit 5.

(Douser 2d)

When the galvano mirror 2c is arranged in the orientation for stopping, irradiation light reach the douser 2d. The douser 2d is a member with materials and/or morphology such that irradiation light is absorbed, for example, and the douser 2d has a function of shutting light.

In the present embodiment, each of the aiming light source 2a and treatment light source 2b generates light continuously. Irradiation light is irradiated on the eye E by arranging the galvano mirror 2c in the orientation for irradiation. On the other hand, irradiation of irradiation light on the eye E is stopped by arranging the galvano mirror 2c in the orientation for stopping.

(Slit Lamp Microscope 3)

The slit lamp microscope 3 is used for observation of an anterior eye part and fundus Ef of the eye E. More specifically, the slit lamp microscope 3 illuminates the eye E with slit light and is used for carrying out magnifying observation of the illuminated area. Here, "observation" includes one or both of observation by eyes and observation of images photographed by an image sensor. The case of observation by eyes is described in the present embodiment; however, in the case in which photographed images are observed, an optical system for photography (photographing system) having the same configuration as conventional slit lamp microscopes is provided.

Figure 2:
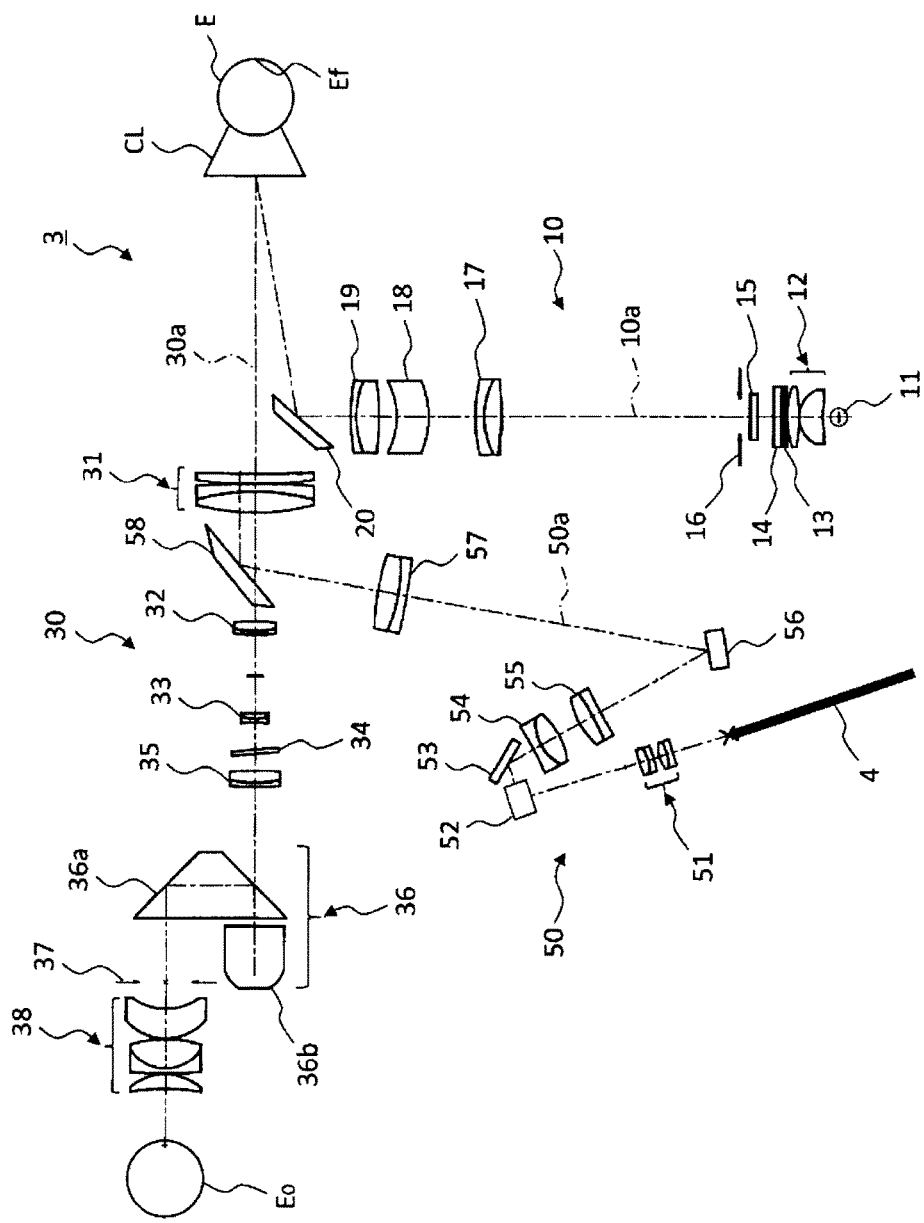
FIG. 2 is a schematic diagram illustrating a configuration example of a laser treatment apparatus according to an embodiment.

The slit lamp microscope 3 includes an illumination part 3a, observation part 3b, eyepiece part 3c and laser-irradiation part 3d. An illumination system 10 shown in FIG. 2 is provided in the illumination part 3a. An observation system 30 is provided in the observation part 3b and eyepiece part 3c. A laser-irradiation system 50 is provided in the laser-irradiation part 3d.

Although illustration is omitted, the slit lamp microscope 3 is provided with same operation members as conventional apparatus such as levers, handles, buttons, knobs, etc. Such operation members are included in the operating unit 6 functionally. In the configuration illustrated in FIG. 1, the processing unit 5 receives signals from the operating unit 6 and controls the slit lamp microscope 3; however, instead of or in addition to such a mechanism that operates by means of electrical driving forces, a mechanism that operates by means of driving forces applied by an operator may be adopted.

(Optical System of Slit Lamp Microscope 3)

An optical system of the slit lamp microscope 3 is described referring to FIG. 2. A contact lens CL used for laser treatment of the fundus Ef is shown in FIG. 2. The slit lamp microscope 3 includes the illumination system 10, observation system 30 and laser-irradiation system 50.

(Illumination System 10)

The illumination system 10 outputs illumination light for observing the eye E. The illumination part 3*a* is capable of changing the direction of an optical axis (illumination optical axis) 10*a* of the illumination system 10 in the crosswise and vertical directions. Thereby, illumination direction of the eye may be arbitrarily changed.

The illumination system 10 includes a light source 11, condensing lens 12, filters 13, 14 and 15, slit diaphragm 16, imaging lenses 17, 18 and 19, and deflecting member 20.

The light source 11 outputs illumination light. A plurality of light sources may be provided in the illumination system 10. For example, it is possible to prepare both of a light source outputting stationary light (halogen lamp, LED, etc.) and light source outputting flash light (xenon lamp, LED, etc.) as the light source 11. Alternatively, a light source for anterior-eye-part observation and light source for fundus observation may be provided separately. The condensing lens 12 is a lens (system) converging light output from the light source 11. Action of the light source 11 is controlled by the processing unit 5.

Each of the filters 13 to 15 is an optical element that removes or weakens specific components of the illumination light. The filters 13 to 15 may be blue filter, red-free filter, light-attenuating filter, thermal protection filter, cornea fluorescence filter, color-temperature changing filter, color-rendering filter, ultraviolet cut filter, infrared cut filter, etc., for example. Each of the filters 13 to 15 may be inserted into/removed from the path of the illumination light. The insertion and removal of the filters 13 to 15 are controlled by the processing unit 5.

The slit diaphragm 16 forms a slit for generating slit light. The slit diaphragm 16 includes a pair of slit blades. The interval of the slit blades is varied to change slit width. Note that any diaphragm member other that the slit diaphragm 16 may be provided in the illumination system 10. Examples of such diaphragm members may be an illumination diaphragm for varying light amount of the illumination light, illumination field diaphragm for varying size of illumination field, etc. The light amount of the illumination light and size of illumination field may be varied by means of members other than these diaphragm members. Examples thereof include a liquid crystal shutter described later. Actions of the slit diaphragm 16, illumination diaphragm, illumination field diaphragm and liquid crystal shutter are controlled by the processing unit 5.

The imaging lenses 17 to 19 are a lens system for forming an image of the illumination light. The deflecting member 20 deflects the illumination light having passed through the imaging lenses 17 to 19 to irradiate it onto the eye E. The deflecting member 20 may be a reflecting mirror or reflecting prism, for example.

Any members other than those described above may be provided in the illumination system 10. For example, a diffuser may be provided after the deflecting member 20 such that the diffuser may be inserted into and removed from the path. The diffuser diffuses the illumination light to make brightness of illumination field uniform. As another example, a background light source that illuminates background of illumination field by the illumination light may be provided.

(Observation System 30)

The observation system 30 is an optical system that guides reflected light of the illumination light from the eye E to the operator's eye $E_O$. The observation system 30 includes a pair of right and left optical systems for binocular observation. The right and left optical systems have substantially the same configurations and only one of them is illustrated in FIG. 2.

The observation part 3*b* is capable of changing the direction of an optical axis (observation optical axis) 30*a* of the observation system 30 in the crosswise and vertical directions. Thereby, observation direction of the eye E may be arbitrarily changed.

The observation system 30 includes an objective lens 31, variable magnification lenses 32 and 33, protection filter 34, imaging lens 35, deflecting part 36, field diaphragm 37 and eyepiece 38.

The objective lens 31 is arranged in a location facing the eye E. The variable magnification lenses 32 and 33 function as a variable magnification optical system (zoom lens system). Each of the variable magnification lenses 32 and 33 may be moved along the observation optical axis 30*a*. As an alternative example of the variable magnification optical system, a plurality of groups of variable magnification lenses selectively insertable in the optical path of the observation system 30 may be provided. The groups of variable magnification lenses apply different powers from each other. A group of variable magnification lenses arranged in the optical path of the observation system 30 is used as the variable magnification lenses 32 and 33. Such variable magnification optical systems may be used to vary magnification (angle of view) of observation images by eyes and photographed images of the eye E. Change of magnification may be carried out by operating an observation-magnification operating knob included in the operating unit 6, for example. The processing unit 5 may control magnification based on operations using switches included in the operating unit 6.

The protection filter 34 is a filter that blocks out the treatment light LT irradiated to the eye E. Thereby, the operator's eye $E_O$ is protected from laser light. The protection filter 34 is inserted into the optical path in response to a trigger for starting laser treatment (or laser emission), for example. At the time of regular observation, the protection filter 34 is removed from the optical path. Insertion/removal of the protection filter 34 is controlled by the processing unit 5. It is possible to use a filter with a multi-layer film structure that reduces change of apparent color tones. Such a filter may be arranged in the optical path at all times.

The imaging lens 35 is a lens (system) that forms an image of the eye E. The deflecting part 36 is an optical member that moves travelling directions of lights parallelly so as to match them with the pupil distance of the operator and includes prisms 36*a* and 36*b*. The eyepiece 38 is moved together with the deflecting part 36. The deflecting part 36 and eyepiece 38 are housed in the eyepiece part 3*c*. Other members of the observation system 30 are housed in the observation part 3*b*.

(Laser-Irradiation System 50)

The laser-irradiation system 50 is an optical system that guides, to the eye E, irradiation light having been transmitted from the light source unit 2 to the slit lamp microscope 3 through the optical fiber 4.

The laser-irradiation system 50 includes a collimator lens 51, galvano scanner 52, mirror 53, relay lenses 54 and 55, mirror 56, collimator lens 57 and deflecting member 58.

The collimator lens 51 converts irradiation light output from the optical fiber 4 into a parallel light flux. The galvano scanner 52 deflects the irradiation light two-dimensionally. The galvano scanner 52 includes a galvano mirror for deflecting the irradiation light in the crosswise direction and galvano mirror for deflecting the irradiation light in the vertical direction. Deflectable directions of reflection surfaces of these galvano mirrors are orthogonal to each other. Two-dimensional deflection is realized by changing orientations of these galvano mirrors independently. Action of the galvano scanner 52 is controlled by the processing unit 5.

The mirror 53 reflects the irradiation light having passed through the galvano scanner 52 to change the travelling direction thereof. The relay lenses 54 and 55 relay the irradiation light reflected by the mirror 53. The mirror 56 reflects the irradiation light having passed through the relay lenses 54 and 55 to change the travelling direction thereof. The collimator lens 57 converts the irradiation light having passed through the relay lenses 54 and 55 into a parallel light flux. The deflecting member 58 is arranged behind the objective lens 31 and deflects the irradiation light having passed through the collimator lens 57 to irradiate it to the eye E.

[Patterns of Irradiation Light]

Patterns of irradiation light are described. There are various conditions for patterns of irradiation light (irradiation conditions). A projection image of irradiation light is referred to as a spot. The irradiation conditions may include any of arrangement of spots (arrangement condition), size of arrangement (arrangement size condition), orientation of arrangement (arrangement orientation condition), size of each spot (spot size condition), intervals between spots (spot interval condition), etc. The number of spots (spot number condition) etc. other than the above may be taken into account; however, such a condition may be identified with other condition (or combination of conditions) substantially.

Figure 3A:
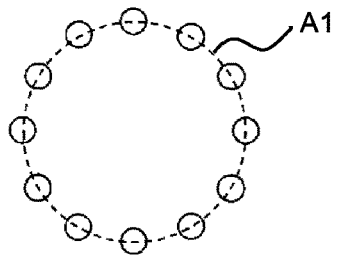
FIG. 3A is a schematic diagram illustrating an example of a pattern of irradiation light from a laser treatment apparatus according to an embodiment.
Figure 3B:
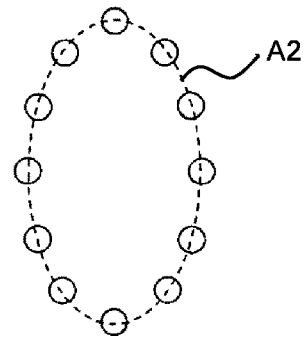
FIG. 3B is a schematic diagram illustrating an example of a pattern of irradiation light from a laser treatment apparatus according to an embodiment.
Figure 3C:
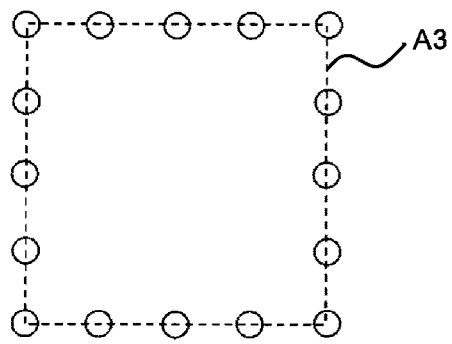
FIG. 3C is a schematic diagram illustrating an example of a pattern of irradiation light from a laser treatment apparatus according to an embodiment.
Figure 3D:
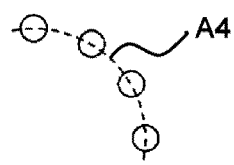
FIG. 3D is a schematic diagram illustrating an example of a pattern of irradiation light from a laser treatment apparatus according to an embodiment.
Figure 3E:
FIG. 3E is a schematic diagram illustrating an example of a pattern of irradiation light from a laser treatment apparatus according to an embodiment.
Figure 3F:
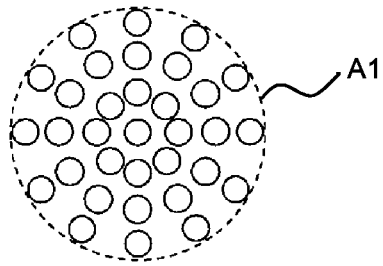
FIG. 3F is a schematic diagram illustrating an example of a pattern of irradiation light from a laser treatment apparatus according to an embodiment.
Figure 3G:
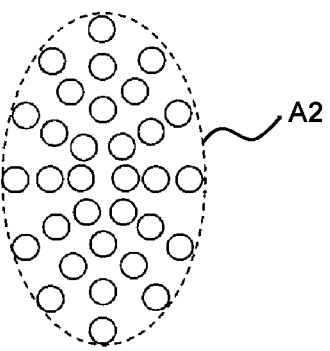
FIG. 3G is a schematic diagram illustrating an example of a pattern of irradiation light from a laser treatment apparatus according to an embodiment.
Figure 3H:
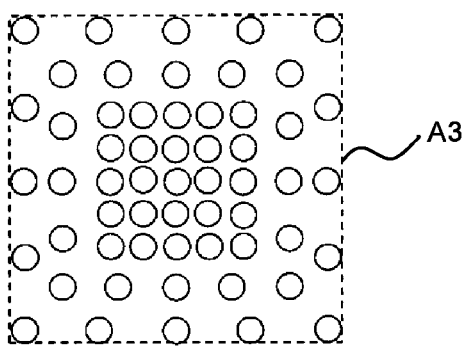
FIG. 3H is a schematic diagram illustrating an example of a pattern of irradiation light from a laser treatment apparatus according to an embodiment.
Figure 3I:
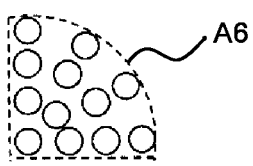
FIG. 3I is a schematic diagram illustrating an example of a pattern of irradiation light from a laser treatment apparatus according to an embodiment.
Figure 3J:
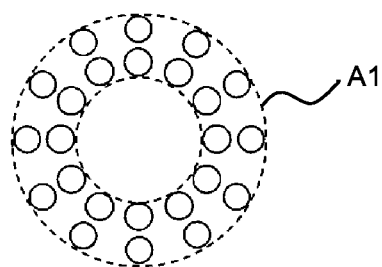
FIG. 3J is a schematic diagram illustrating an example of a pattern of irradiation light from a laser treatment apparatus according to an embodiment.
Figure 3K:
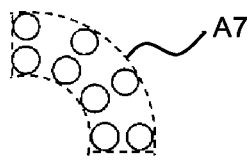
FIG. 3K is a schematic diagram illustrating an example of a pattern of irradiation light from a laser treatment apparatus according to an embodiment.
Figure 3L:
FIG. 3L is a schematic diagram illustrating an example of a pattern of irradiation light from a laser treatment apparatus according to an embodiment.

The arrangement condition indicates how a plurality of spots is arranged. There are various arrangement conditions as described in the patent documents cited above. As specific examples, there are circular arrangement (FIG. 3A), elliptic arrangement (FIG. 3B), rectangular arrangement (FIG. 3C), arc-shaped arrangement (FIG. 3D), linear arrangement (FIG. 3E), disc-shaped arrangement (FIG. 3F), elliptic-plate-shaped arrangement (FIG. 3G), rectangular-plate-shaped arrangement (FIG. 3H), fan-plate-shaped arrangement (FIG. 3I), circular arrangement with width (annulus-ring-shaped arrangement (FIG. 3J)), arc-shaped arrangement with width (a part of annulus-ring-shaped arrangement or partial annulus-ring-shaped arrangement (FIG. 3K)), and linear arrangement with width (strip-shaped arrangement (FIG. 3L)). Further, the user may set arrangements arbitrarily. Moreover, a combination of two or more arrangements may be applied (such as FIG. 6(h) in the Patent Document 1). The arrangement conditions are used for controlling the galvano scanner 52.

The arrangement size condition of a certain arrangement indicates a size of the arrangement to be projected. A parameter indicating a size (such as diameter) of the circular arrangement is one example of the arrangement size condition. It is possible to set arrangement size condition arbitrarily and/or to prepare their choices (such as large, medium, small). The arrangement size conditions are used for controlling the galvano scanner 52.

The arrangement orientation condition of a certain arrangement indicates an orientation of the arrangement to be projected. A parameter indicating an orientation of the arc-shaped arrangement is one example of the arrangement orientation condition. It is possible to set arrangement orientation condition arbitrarily and/or to prepare their choices (such as up, down, left, right). The arrangement orientation conditions are used for controlling the galvano scanner 52.

The spot size condition indicates a size of spots to be projected. For example, regarding the circular arrangement, circular arrangements of different patterns may be applied by changing projection sizes (diameters, areas, perimeters, etc.) of the respective spots. It is possible to set spot size condition arbitrarily and/or to prepare their choices (such as large, medium, small). Note that regarding a certain arrangement, all the spot sizes may not be the same. In such a case, it is possible to divide a certain arrangement into two or more parts and set spot sizes for the respective parts individually.

Configurations for changing spot sizes are described. In the case in which the optical fiber 4 has a single light guide, the laser-irradiation system 50 is provided with an optical member(s) for changing spot sizes. Such an optical member(s) may be a variable magnification lens (system). The processing unit 5 moves the variable magnification lens along an optical axis (irradiation optical axis) 50a of the laser-irradiation system 50, thereby realizing a set spot size.

In the case in which the optical fiber 4 has two or more single light guides, the light guides may have different diameters. In such a case, the spot size of light irradiated to the eye E is varied by selectively using the light guides. The processing unit 5 arranges the galvano mirror 2c of the light source unit 2 in a direction such that irradiation light is entered a light guide corresponding to a selected spot size.

The optical fiber 4 may be an image fiber that is capable of transmitting light with maintaining its pattern. In such a case, an optical member(s) for changing spot sizes (such as a variable magnification lens) is provided at an arbitrary position before or after the optical fiber 4. Control of this optical member is similar to the case of the optical fiber 4 with a single light guide.

The spot interval condition indicates intervals of adjacent spots to be projected. It is possible to set spot interval condition arbitrarily and/or to prepare their choices (such as sparse, dense). Note that regarding a certain arrangement, all the spot intervals may not be the same. In such a case, it is possible to divide a certain arrangement into two or more parts and set spot intervals for the respective parts individually. The spot interval conditions are used for controlling the galvano scanner 52.

The irradiation conditions may include conditions regarding items other than patterns of irradiation light. For example, in the case in which a plurality of kinds of irradiation light may be applied selectively, kinds of irradiation light may be included in the irradiation conditions. Specific examples of kinds of irradiation light include kinds of laser light (such as wavelengths, usages, etc.). Such irradiation light kind conditions are used for controlling the aiming light source 2a and/or treatment light source 2b.

The irradiation conditions may include conditions regarding intensity of irradiation light. Specific examples of such irradiation intensity conditions include output intensity conditions indicating intensities of irradiation light output by the aiming light source 2a and/or treatment light source 2b. The output intensity conditions are used for controlling the aiming light source 2a and/or treatment light source 2b. The output intensity conditions may include parameters indicating energy of treatment light (laser light) output from the treatment light source 2b.

Another example of the irradiation intensity conditions is a condition (light attenuation condition) for adjusting light amount of irradiation light by means of a light-attenuating member. The light-attenuating member may be a light-attenuating filter. More specifically, it is possible to apply a configuration in which a single light-attenuating filter are inserted into/removed from the optical path or a configuration in which a plurality of light-attenuating filters with different transmittances are selectively arranged in the optical path.

[Control System]

Figure 4:
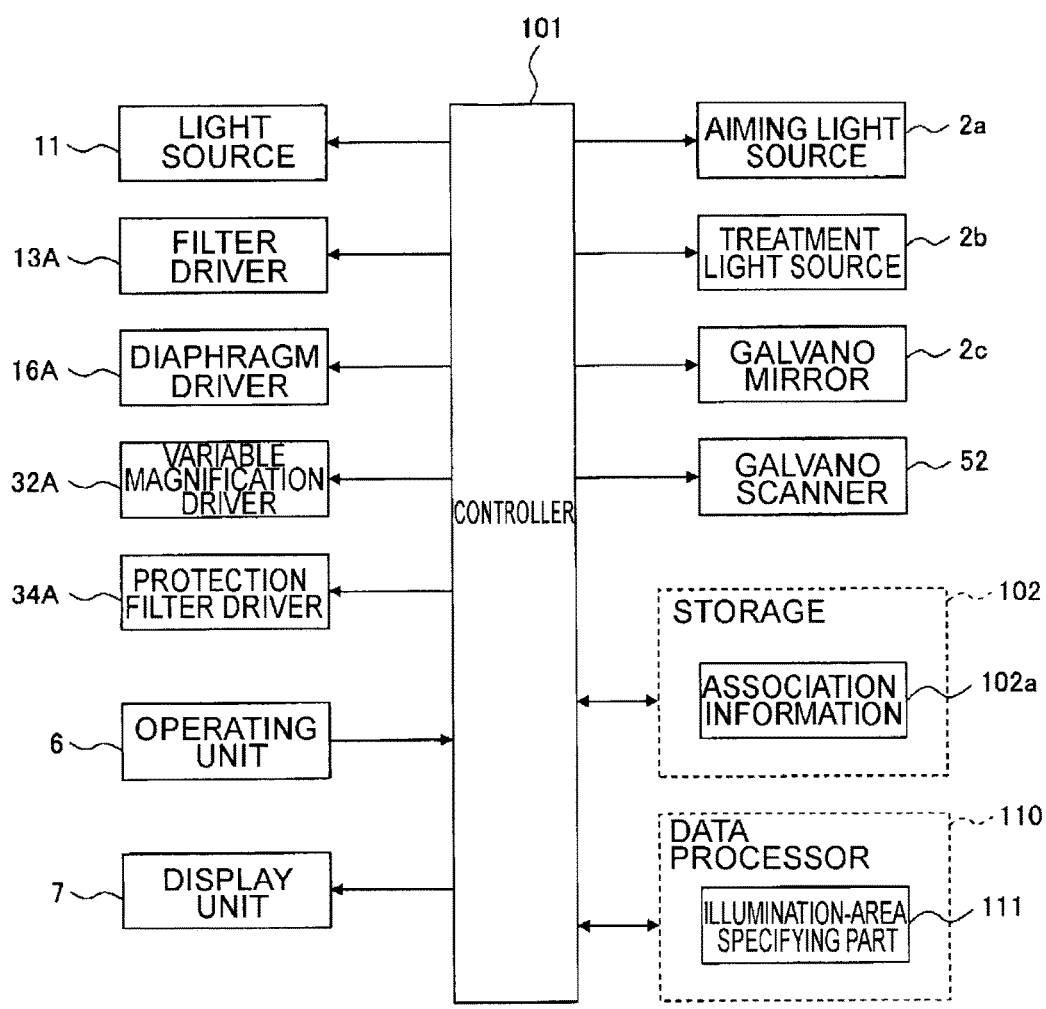
FIG. 4 is a schematic diagram illustrating a configuration example of a laser treatment apparatus according to an embodiment.

A control system of the laser treatment apparatus 1 is described referring to FIG. 4. The center of the control system of the laser treatment apparatus 1 is a controller 101 provided in the processing unit 5. FIG. 4 shows components especially concerned only and other component are omitted.

(Controller 101)

The controller 101 controls each part of the laser treatment apparatus 1. For example, the controller 101 performs controls of the light source unit 2, display unit 7, illumination system 10, observation unit 30, laser-irradiation system 50, etc.

As controls of the light source unit 2, the controller 101 performs controls of the aiming light source 2a, treatment light source 2b, galvano mirror 2c. The controls of the aiming light source 2a and treatment light source 2b include turning on/off of output of irradiation light, control of output intensity (output light amount) of irradiation light, etc. In the case in which one or more treatment light sources 2b output a plurality of kinds of treatment light LT, the controller 101 controls the treatment light sources 2b so as to output treatment light LT selectively. The controls of the galvano mirror 2c include a control for changing orientation of the reflecting surface of the galvano mirror 2c.

The display unit 7 displays various kinds of information upon receiving control from the controller 101. The display unit 7 includes an arbitrary display device such as a flat panel display (LCD etc.), CRT display, and the like. The display unit 7 is provided in the slit lamp microscope 3 or processing unit 5 (computer), for example.

As controls of the illumination system 10, the controller 101 performs controls or the light source 11, filters 13 to 15, slit diaphragm 16, other diaphragm members. The controls of the light source 11 include turning on/off of output of illumination light, control of output intensity (output light amount) of illumination light, etc.

The controls of the filters 13 to 15 include controls of inserting/removing the filters 13 to 15 into/from the illumination optical axis 10a independently. The controls of the filters 13 to 15 are executed by controlling a filter driver 13A. The filter driver 13A includes an actuator(s) such as a solenoid or pulse motor and a mechanism that transmits driving force generated by the actuator to the filters 13 to 15.

The controls of the slit diaphragm 16 include control of changing interval between the pair of slit blades and control of moving the pair of slit blades integrally. The former control corresponds to control of changing the slit width. The latter control corresponds to control of changing irradiation position of illumination light (slit light) with maintaining the slit width constant. The other diaphragm members may be the illumination diaphragm for varying light amount of the illumination light, illumination field diaphragm for varying size of illumination field, etc. as described above. Controls of the slit diaphragm 16, illumination diaphragm and illumination field diaphragm are independently performed by controlling a diaphragm driver 16A. The diaphragm driver 16A includes an actuator(s) such as a pulse motor and a mechanism that transmits driving force generated by the actuator to the diaphragm members.

As controls of the observation system 30, the controller 101 performs controls of the variable magnification lenses 32 and 33 and protection filter 34. The controls of the variable magnification lenses 32 and 33 include control of a variable magnification driver 32A for moving them along the observation optical axis 30a or for arranging the groups of variable magnification lenses with different powers in the optical path of the observation system 30. Thereby, observation magnification (angle of view) is varied. The variable magnification driver 32A includes an actuator(s) such as a pulse motor and a mechanism that transmits driving force generated by the actuator to the variable magnification lenses 32 and 33. The controls of the protection filter 34 are control of a protection filter driver 34A for inserting/removing the protection filter 34 into/from the observation optical axis 30a.

As controls of the laser-irradiation system 50, the controller 101 performs control of the galvano scanner 52 etc. As described above, the galvano scanner 52 includes the galvano mirror (first galvano mirror) for deflecting irradiation light in the crosswise direction and galvano mirror (second galvano mirror) for deflecting irradiation light in the vertical direction. The controller 101 controls orientations of the reflecting surfaces of the first and second galvano mirrors independently. Thereby, it is possible to deflect irradiation light entered from the light source unit 2 via the optical fiber 4 two-dimensionally.

The controller 101 reads out data stored in storage 102 and writing data into the storage 102.

The controller 101 includes a microprocessor, RAM, ROM, hard disk drive, etc. The hard disk drive stores control programs in advance. Actions of the controller 101 are realized by cooperation of the control programs and hardware described above. The controller 101 may include a communication device for communicating with external apparatuses. The controller 101 is included in a "controller".

(Storage 102)

The storage 102 stores various data and computer programs. The storage 102 includes storage devices such as RAM, ROM, hard disk drive etc. The storage 102 is included in a "controller".

The storage 102 stores association information 102a in advance. Irradiation conditions of irradiation light generated by the light source unit 2 and illumination areas of fundus by the illumination system 10 are associated with each other in the association information 102a. As described above, irradiation light with a preset pattern is irradiated on the fundus Ef in the present embodiment, and the irradiation conditions of irradiation light may include arrangement condition indicating arrangement of spots forming a preset pattern, arrangement size condition indicating size of a preset pattern, arrangement orientation condition indicating orientation of a preset pattern, spot size condition indicating size of respective spots, spot interval condition indicating intervals between spots, etc. Further, the illumination area by the illumination system 10 is varied by means of the diaphragm members described above (slit diaphragm 16, illumination diaphragm, illumination field diaphragm) and the like. The association information 102a associates one or a combination of two or more of the above irradiation condition(s) with illumination area by the illumination system 10.

Figure 5:
FIG. 5 is a schematic diagram illustrating a configuration example of a laser treatment apparatus according to an embodiment.

Specific examples of the association information 102a are described. The association information 102a shown in FIG. 5 is table information in which arrangement conditions and illumination areas are associated with each other. As the arrangement conditions, circular arrangement, elliptic arrangement, rectangular arrangement, arc-shaped arrangement, linear arrangement, disc-shaped arrangement, elliptic-plate-shaped arrangement, rectangular-plate-shaped arrangement, fan-plate-shaped arrangement, annulus-ring-shaped arrangement, partial annulus-ring-shaped arrangement and strip-shaped arrangement described above are listed. Each illumination area is set so as to include associated arrangement condition (and size of pattern), for example. Information indicating opening sizes of the diaphragm members (such as slit width, slit length, etc.) are used as parameters of the respective illumination areas. Examples of such parameters include position information of slit blades of the slit diaphragm 16, values of slit width, values of slit length, F-number (F-value) of the illumination field diaphragm, etc.

A preset illumination area A1 is associated with the circular arrangement in which a plurality of spots is arranged in a circle, and with the disc-shaped arrangement and annulus-ring-shaped arrangement obtained by providing spots inside the circular arrangement. A preset illumination area A2 is associated with the elliptic arrangement in which a plurality of spots is arranged in an ellipse, and with the elliptic-plate-shaped arrangement obtained by providing spots inside the elliptic arrangement. A preset illumination area A3 is associated with the rectangular arrangement in which a plurality of spots is arranged in a rectangle, and with the rectangular-plate-shaped arrangement obtained by providing spots inside the rectangular arrangement. A preset illumination area A4 is associated with the arc-shaped arrangement in which a plurality of spots is arranged in an arc. A preset illumination area A5 is associated with the linear arrangement in which a plurality of spots is arranged in a line. A preset illumination area A6 is associated with the fan-plate-shaped arrangement in which a plurality of spots is arranged in a two-dimensional region with a fan-shaped contour. A preset illumination area A7 is associated with the partial annulus-ring-shaped arrangement in which a plurality of spots is arranged in a two-dimensional region that is a part of the annulus-ring-shaped arrangement. A preset illumination area A8 is associated with the strip-shaped arrangement in which a plurality of spots is arranged in a two-dimensional region obtained by enlarging the linear arrangement in its short direction. Each of the illumination areas A1 to A8 is set in advance according to shape and/or size of associated arrangement condition, for example. Sizes of arrangement conditions (sizes of patterns of irradiation light) may be default values (standard sizes) arbitrarily set.

The association information 102a in which arrangement size conditions are taken into account is described. The arrangement size conditions are set as ratios to standard sizes of the respective patterns of irradiation light, for example. As a specific example, in the case in which standard sizes are set in advance as described regarding the association information 102a of FIG. 5, association information 102a in which values indicating ratios of sizes of patterns to the standard sizes are associated with parameters indicating illumination areas is created. In the case in which whole sizes of patterns (that is, arrangement size conditions) are changed according to change of spot size conditions, spot interval conditions, etc., association information 102a is created by taking spot size conditions, spot interval conditions, etc. into consideration in the same way as the above.

The association information 102a in which arrangement orientation conditions are taken into account is described. The association information 102a in which arrangement orientation conditions are taken into account is not necessarily set for arrangement patterns having rotational symmetry. For example, since the circular and disc-shaped arrangements are symmetric regarding any rotations, they are not necessarily included in items of the arrangement orientation conditions. In contrast, the elliptic and elliptic-plate-shaped arrangements are symmetric only for 180-degree rotation. Therefore, association information 102a in which different illumination areas are associated with changes of arrangement orientation conditions, that is, with various values of rotation degrees. The same applies to other arrangements.

(Operating Unit 6 and Display Unit 7)

The operating unit 6 includes various kinds of hardware keys and/or software keys as described above. The display unit 7 displays various kinds of information. As described later, the operating unit 6 (and the display unit 7) functions as examples of an "irradiation-condition setting part" and "operation part".

The operating unit 6 is used for setting irradiation conditions of irradiation light. Operations for setting irradiation conditions are performed by means of predetermined hardware keys or software keys, for example. As an example of the former, the operating unit 6 is provided in advance with hardware keys for setting any irradiation conditions such as arrangement conditions, arrangement size conditions, arrangement orientation conditions, spot size conditions, spot interval conditions, spot number conditions, irradiation light kind conditions, irradiation intensity conditions (output intensity conditions, light attenuation conditions), etc. The user operates hardware keys corresponding to a desired irradiation conditions to set irradiation conditions. As an example of the latter, the controller 101 controls the display unit 7 to display a setting screen for setting irradiation conditions described above. The user operates GUI provided in the displayed setting screen by means of the operating unit 6 to set irradiation conditions.

The operating unit 6 is used for changing irradiation position of irradiation light on the fundus Ef. Such operations for moving irradiation position are also performed by means of a predetermined hardware keys or software keys. Movement of irradiation position is carried out by the controller controlling the galvano scanner 52 or by moving the optical system of the slit lamp microscope 3, for example. In the latter case, the slit lamp microscope 3 is provided with a moving mechanism for moving the optical system (optical system moving mechanism). The optical system moving mechanism is electrically controlled and includes an actuator and a mechanism that transmits driving force generated by the actuator. It is also possible to configure in which the optical system of the slit lamp microscope 3 is moved by driving force generated by user's manipulations.

FIG. 4 illustrates an example in which the operating unit 6 and display unit 7 are separated; however, they may be configured integrally. A specific example thereof is a touch panel LCD.

(Data Processor 110)

A data processor 110 executes various kinds of data processing. The data processor 110 is provided with an illumination-area specifying part 111.

(Illumination-Area Specifying Part 111)

The illumination-area specifying part 111 specifies an illumination area associated with an irradiation condition set by means of the operating unit 6 (and display unit 7). The illumination-area specifying part 111 is included in the "controller". Specific examples of processing executed by the illumination-area specifying part 111 are described.

When an irradiation condition such as arrangement conditions, arrangement size conditions, arrangement orientation conditions, spot size conditions, spot interval conditions, spot number conditions, irradiation light kind conditions, irradiation intensity conditions (output intensity conditions, light attenuation conditions), etc. is set, the illumination-area specifying part 111 specifies an illumination area associated with the set irradiation condition based on the association information 102a. Such specification is executed by searching an illumination area associated with the set irradiation condition in the association information 102a as shown in FIG. 5, for example. For instance, when "circular arrangement" is set as arrangement condition, the illumination area "A1" associated with "circular arrangement" in the association information 102a as shown in FIG. 5 is specified.

Note that there are cases in which a plurality of items (arrangements) are selected and set. Such cases are classified into cases in which one of a plurality of arrangements includes others and otherwise. When arrangement condition consisting of a combination of a plurality of arrangements is set, the illumination-area specifying part 111 judges inclusion relation of these arrangements. When one arrangement including others is specified, the illumination-area specifying part 111 specifies an illumination area corresponding to this one arrangement based on the association information 102a.

On the other hand, when such one arrangement is not specified, the illumination-area specifying part 111 specifies two or more arrangements included in the concerned combinational arrangement condition. Two or more arrangements specified here is an arrangement consisting of outer edge (contour) of the pattern indicated by this combinational arrangement condition, for example. Next, the illumination-area specifying part 111 specifies illumination areas associated with the specified two or more arrangements respectively based on the association information 102a and determines a new illumination area that includes at least these illumination areas. The new illumination area is used as the result of specification by the illumination-area specifying part 111.

When irradiation position of irradiation light is moved, the illumination-area specifying part 111 obtains an illumination area corresponding to moving operation of irradiation position by means of the operating unit 6. Such processing is described more specifically. Moving operation of irradiation position is performed when irradiation light (in particular, aiming light) is being irradiated. In the case in which movement of irradiation position is performed via the controller 101, the controller 101 transmits control contents for the galvano scanner 52 or optical system moving mechanism to the illumination-area specifying part 111. The illumination-area specifying part 111 specifies direction and amount of movement of illumination area based on the control contents (that is, content of movement of irradiation position).

On the other hand, in the case in which irradiation position is moved by user's manipulation as driving force, the illumination-area specifying part 111 is provided with a detector that detects operation contents of user or movement contents of the optical system. The detector may include an encoder that detects operation contents or a position sensor that detects position of the optical system. The illumination-area specifying part 111 specifies direction and amount of movement of illumination area based on detection result from the detector.

The illumination-area specifying part 111 transmits specification result of illumination area obtained as above to the controller 101. The controller 101 controls the diaphragm members (slit diaphragm 16 etc.) based on the specification result of illumination area to change illumination area of the fundus Ef by the illumination system 10.

[Actions]

Figure 6:
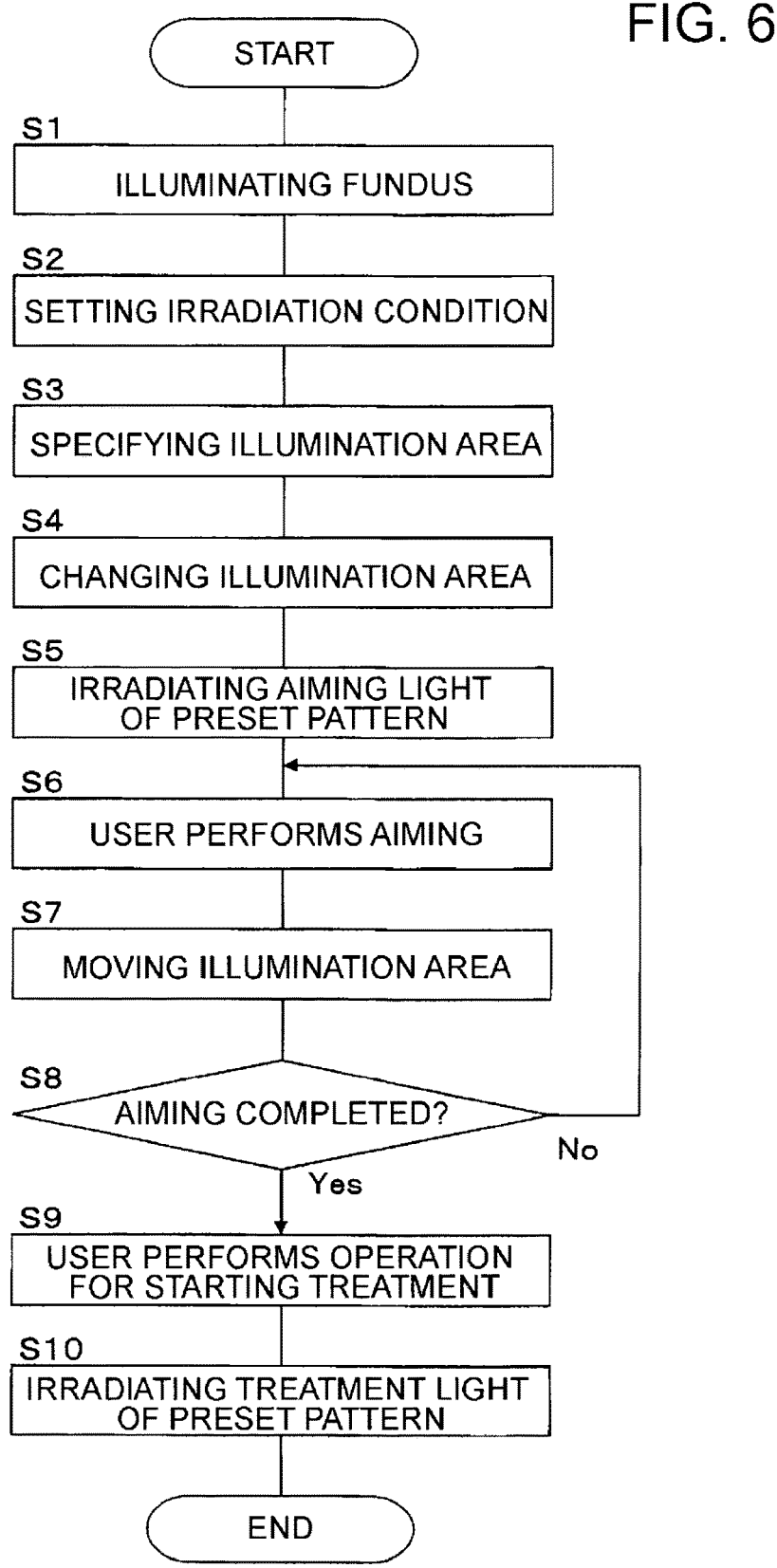
FIG. 6 is a flowchart illustrating an action example of a laser treatment apparatus according to an embodiment.

Actions of the laser treatment apparatus 1 are described. FIG. 6 illustrates an example of an action of the laser treatment apparatus 1. It is assumed that the contact lens CL is in contact with the eye E.

(S1: Illuminating Fundus)

In response to a predetermined operation by the user, the controller 101 turns on the light source 11 of the illumination system 10. At this time, the diaphragm members such as the slit diaphragm 16 are in initial states. Thereby, the fundus Ef of the eye E is illuminated by illumination light.

(S2: Setting Irradiation Condition)

The user sets irradiation condition of the aiming light LA and/or treatment light LT. This setting operation is performed by means of the irradiation-condition setting part such as the operating unit 6. Signals indicating setting contents of irradiation conditions are transmitted to the illumination-area specifying part 111 via the controller 101.

(S3: Specifying Illumination Area)

The illumination-area specifying part 111 specifies an illumination area corresponding to the irradiation condition set in Step 2 based on the association information 102a. This processing is described above. The illumination-area specifying part 111 transmits signals indicating the specified illumination area to the controller 101.

(S4: Changing Illumination Area)

The controller 101 controls the diaphragm driver 16A based on the illumination area specified in Step 3 to change illumination area of the fundus Ef by the illumination system 10. Such change of illumination area is scale-up or scale-down by changing slit width of the slit diaphragm 16, for example.

(S5: Irradiating Aiming Light of Preset Pattern)

Upon the user performs a predetermined operation, the controller 101 controls the aiming light source 2a, galvano mirror 2c, galvano scanner 52, etc. to irradiate the aiming light LA of a preset pattern on the fundus Ef. Commencement timing of irradiation of aiming light may be arbitrary after Step 2. The pattern of the aiming light LA is based on the irradiation condition (arrangement condition etc.) set in Step 2, for example.

(S6: User Performs Aiming)

The user observes fundus tissues in the illumination area by the illumination system 10 to recognize sites for treatment (lesions) and moves irradiation position of the aiming light LA such that the aiming light LA is irradiated on the sites for treatment. This operation is performed by means of the operation part such as the operating unit 6.

As described above, the illumination area of the fundus Ef after the change in Step 4 includes irradiation position (projection pattern) of the aiming light LA irradiated on the fundus Ef in Step 5. Therefore, the user (operator) can observe at least the irradiation position of the aiming light LA and judge whether or not the irradiation position matches the sites for treatment. Aiming is not required when the irradiation position matches the sites for treatment; however, such cases are rare. So, aiming is performed as above in actual cases.

(S7: Moving Illumination Area)

Operation contents for aiming in Step 6, that is, movement contents of irradiation position of the aiming light LA is recognized by the controller 101 in the way described above. The controller 101 controls the diaphragm driver 16A in response to operation of moving irradiation position of the aiming light LA to change illumination area of the fundus Ef by the illumination system 10. This change of illumination area is movement of illumination area by moving the pair of slit blades of the slit diaphragm 16 with maintaining the slit width constant, that is, tracking of illumination area with respect to irradiation position, for example. The change of illumination area may be transfer to a new illumination area including the irradiation position of the aiming light LA after movement. The change of illumination area may be enlargement of illumination area such that the irradiation positions of the aiming light LA both before and after movement.

(S8: Aiming Completed?)

Steps 6 and 7 are repeated until aiming is completed (S8: No, S6, S7).

(S9: User Performs Operation for Starting Treatment)

After aiming is completed (S8: Yes), the user performs a predetermined operation for starting treatment by means of the operating unit 6.

(S10: Irradiating Treatment Light of Preset Pattern)

In response to the operation for starting treatment, the controller 101 stops irradiation of the aiming light LA to the eye E and controls the treatment light source 2b, galvano mirror 2c, galvano scanner 52 etc. to irradiate the treatment light LT of a preset pattern on the fundus Ef.

The pattern of the treatment light LT may be the same as the pattern of the aiming light LA or different. As an example of the latter, the treatment light LT of a pattern that is a part of the pattern of the aiming light LA may be irradiated. Spot sizes, spot intervals, etc. may be changed. This completes the description of the example of action.

[Effects]

Effects of the laser treatment apparatus 1 are described.

The laser treatment apparatus 1 includes the illumination system 10, observation system 30, irradiation system (light source unit 2 and laser-irradiation system 50), illumination-area changing part (diaphragm members such as slit diaphragm 16 etc.), irradiation-condition setting part (operating unit 6 etc.) and controller 101. The illumination system 10 illuminates the fundus Ef of the eye E. The observation system 30 is used for observing the fundus Ef illuminated by the illumination system 10. The irradiation system irradiates aiming light LA of a preset pattern and treatment light LT consisting of laser light of a pattern determined based on the preset pattern of the aiming light LA onto the fundus Ef. As described above, the pattern of the treatment light LT may be the same as that of the aiming light LA or different. The illumination-area changing part changes an illumination area of the fundus Ef by the illumination system 10. The irradiation-condition setting part is used for setting irradiation condition of the aiming light LA and/or treatment light LT from the irradiation system. The controller controls the illumination-area changing part based on the irradiation condition set by the irradiation-condition setting part to change the illumination area of the fundus Ef by the illumination system 10.

According to such a laser treatment apparatus 1, illumination area of the fundus Ef can be changed automatically in accordance with irradiation conditions of the aiming light LA and treatment light LT. Thereby, it is possible to take the hassle out of adjusting illumination area and facilitate operations of a laser treatment apparatus.

The irradiation conditions of irradiation light (aiming light LA and treatment light LT) may include one or more or the following conditions: arrangement of spots in patterns of irradiation light; size of patterns of irradiation light; orientation of patterns of irradiation light; size of spots in patterns of irradiation light; and intervals of spots in patterns of irradiation light. According to such a configuration, illumination area may be changed automatically regarding various irradiation conditions.

The irradiation-condition setting part may include the operation part (operating unit 6 etc.) for moving irradiation positions of the aiming light LA on the fundus Ef. If this is the case, the controller 101 may change illumination area according to movement operation of the irradiation position by means of the operation part. According to such a configuration, it is possible to take the hassle out of operations for changing illumination area associated with movement of irradiation position of the aiming light LA, thereby further facilitating operations of a laser treatment apparatus.

MODIFICATION EXAMPLES

Embodiments described above are merely illustrations for implementing the present invention. Therefore, arbitrary modifications (omission, replacement, addition, etc.) may be made within the scope of the present invention. Examples of modifications are described below. Note that any configurations included in the above embodiments and any configurations included in the following modification examples may be combined in an arbitrary way.

Modification Example 1

The above embodiment describes a case in which diaphragm members such as the slit diaphragms 16 etc. are used as the illumination-area changing part. This modification example describes a case in which liquid crystal shutter is used as the illumination-area changing part.

Figure 7:
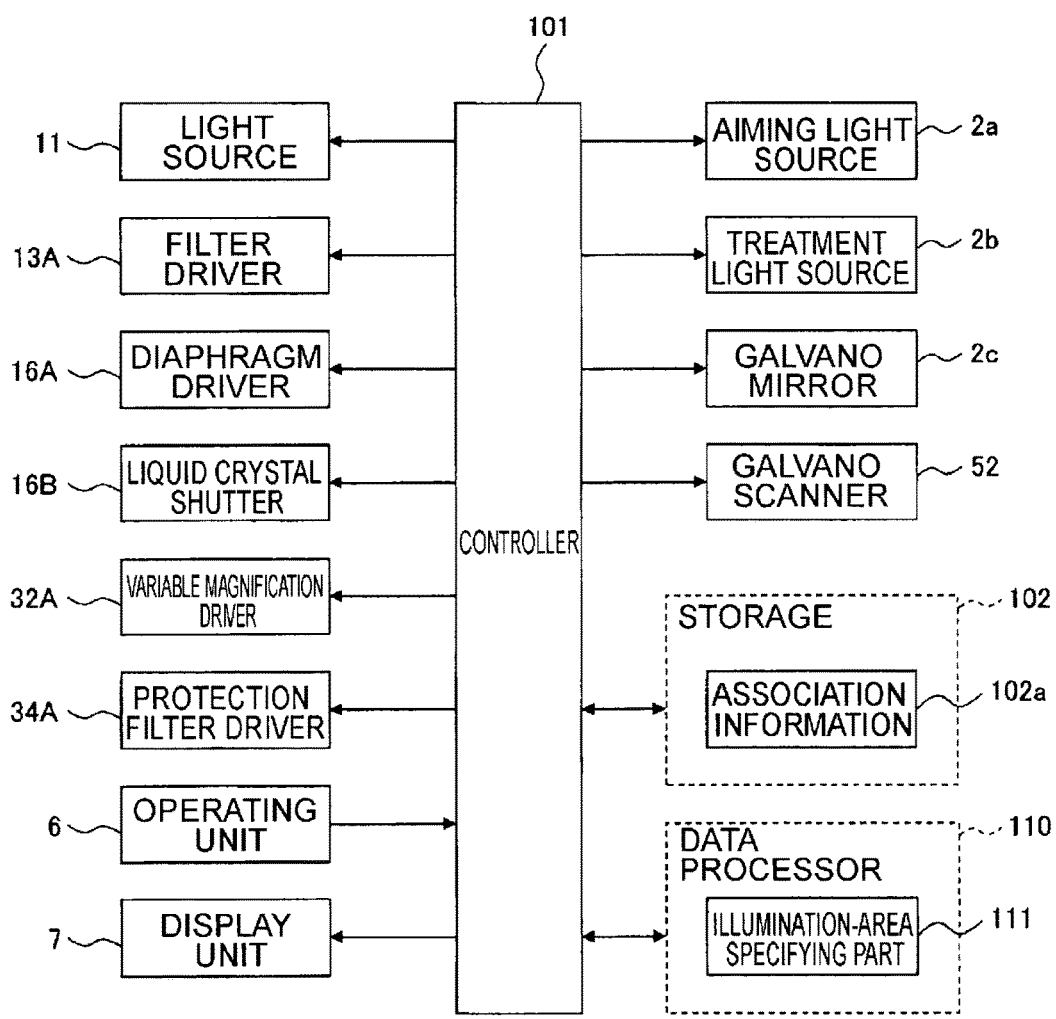
FIG. 7 is a schematic diagram illustrating a configuration example of a modified example of a laser treatment apparatus according to an embodiment.

FIG. 7 illustrates a configuration example of a laser treatment apparatus according to the present modification example. A laser treatment apparatus according to the present modification example includes configurations in which a liquid crystal shutter 16B is added to the configuration of the above embodiment. The liquid crystal shutter 16B has a configuration in which a liquid crystal cell plate and polarizing plate are stacked, for example, and receives electrical controls to the liquid crystal cell plate to perform open/close of shutter, change of light-transmitting region, change of light-transmittance, etc. Such actions of the liquid crystal shutter 16B are controlled by the controller 101.

Switch on/off of illumination to the fundus Ef, change of illumination area, change of brightness of illumination may be performed by controlling the liquid crystal shutter 16B. In particular, in the present modification example, the controller 101 may control the liquid crystal shutter 16B based on the irradiation condition set by the irradiation-condition setting part (operating unit 6 etc.) to change illumination area of the fundus Ef by the illumination system 10. According to such a configuration, it is possible to automatically change illumination area of the fundus Ef in accordance with irradiation conditions of the aiming light LA and treatment light LT, thereby taking the hassle out of adjusting illumination area and facilitating operations of a laser treatment apparatus.

Modification Example 2

The above embodiment and modification example 1 describe cases in which illumination area of the fundus Ef is changed by processing illumination light output from the light source 11. The present modification example describes a configuration that controls a light source itself to change illumination area of the fundus Ef.

Figure 8:
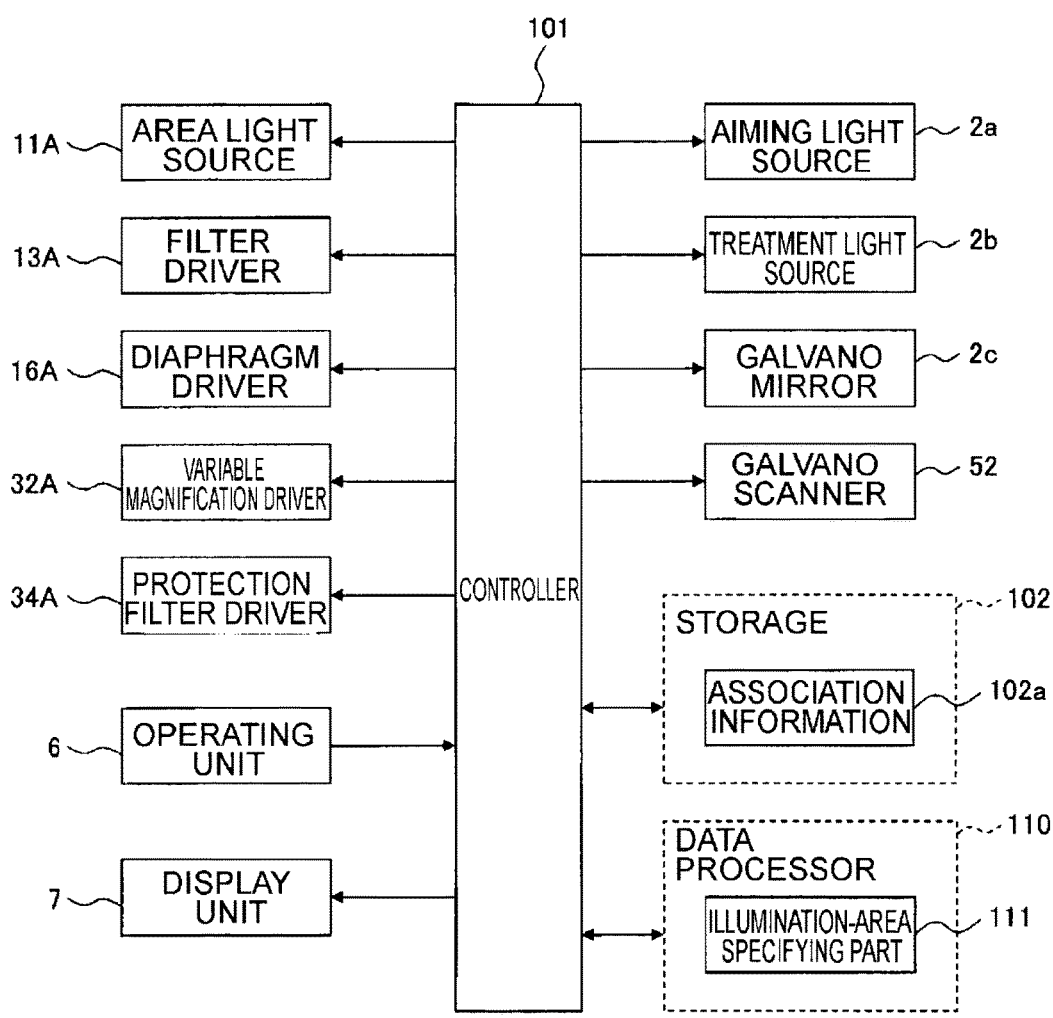
FIG. 8 is a schematic diagram illustrating a configuration example of a modified example of a laser treatment apparatus according to an embodiment.

FIG. 8 illustrates a configuration example of a laser treatment apparatus according to the present modification example. A laser treatment apparatus according to the present modification example has a configuration in which the light source 11 of the above embodiment is replaced by an area light source 11A. The area light source 11A generates illumination light from a planar or curved-surface-shaped light-emitting surface. The area light source 11A may be a light source that emits light from one surface such as an organic EL display or may be a light source unit in which a plurality of light sources (LED etc.) is arranged two-dimensionally.

The controller controls the area light source 11A to change light-emitting area. When the area light source 11A is an organic EL display for example, light-emitting area of the area light source 11A may be changed by selectively lighting a plurality of light emitters configuring a backlight. Alternatively, when the area light source 11A is the light source unit described above, light-emitting area of the area light source 11A may be changed by selectively lighting the plurality of light sources.

The controller 101 controls the area light source 11A (illumination-area changing part) based on irradiation condition set by the irradiation condition setting part to output illumination light from light-emitting area corresponding to the irradiation condition. Correspondence between irradiation conditions and light-emitting areas may be obtained by creating association information 102a similar to the above embodiment in advance, for example.

Illumination area of the fundus Ef by the illumination system 10 is changed by changing light-emitting area of the area light source 11A in such a way. Accordingly, it is possible to automatically change illumination area of the fundus Ef in accordance with irradiation conditions of the aiming light LA and treatment light LT, thereby taking the hassle out of adjusting illumination area and facilitating operations of a laser treatment apparatus.

Modification Example 3

The above embodiment and modification examples describe cases in which irradiation conditions are set by means of the irradiation-condition setting part such as the operating unit 6. The present modification example describes a configuration capable of setting irradiation conditions automatically.

Figure 9:
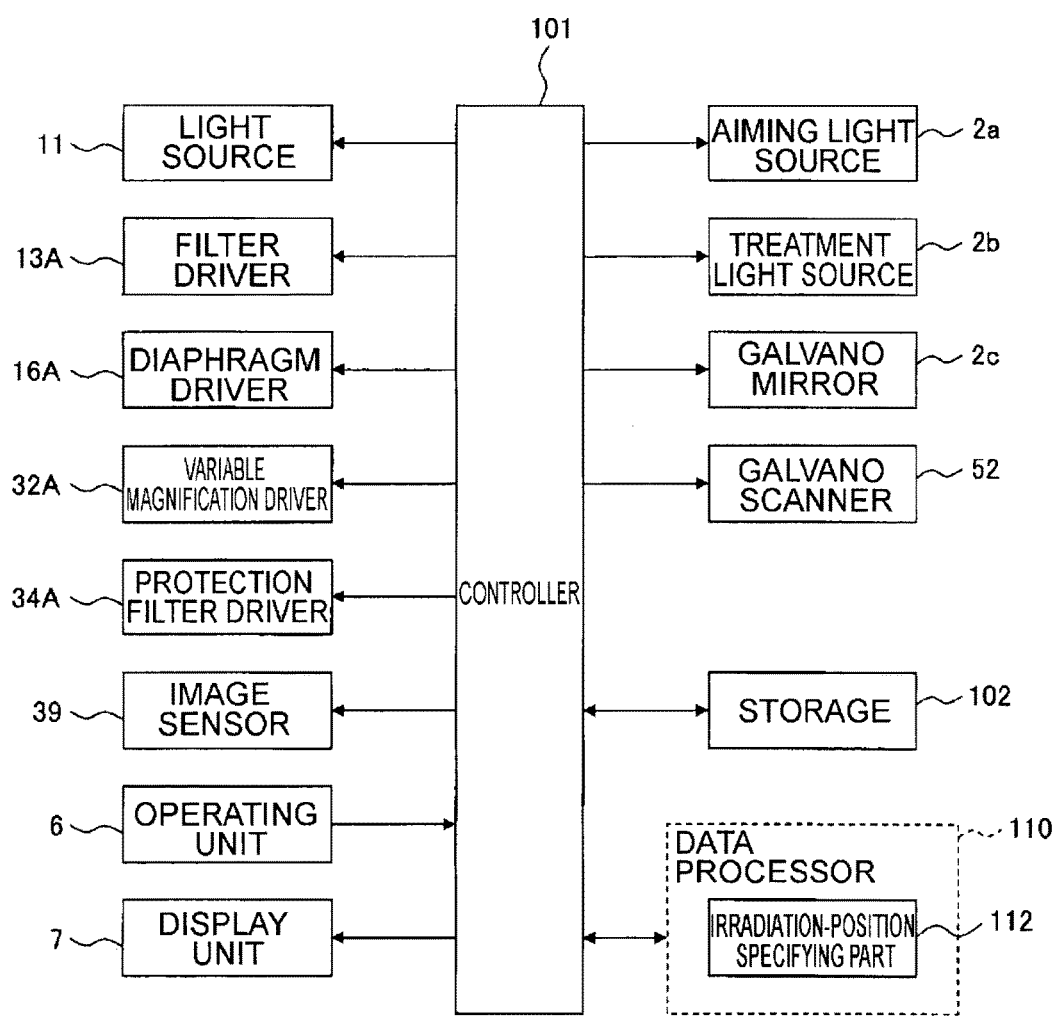
FIG. 9 is a schematic diagram illustrating a configuration example of a modified example of a laser treatment apparatus according to an embodiment.

FIG. 9 illustrates a configuration example of a laser treatment apparatus according to the present modification example. A laser treatment apparatus according to the present modification example includes an image sensor 39 in the observation system 30 and irradiation-position specifying part 112 in the data processor 110.

The image sensor 39 is provided on an optical path branched from the observation optical axis 30a, for example. This branching may be realized by means of a beam splitter such as a half mirror. The image sensor 39 is sensitive in wavelength bands of irradiation light (aiming light LA and treatment light LT). When the image sensor 39 performs photography in a state in which irradiation light is being irradiated on the fundus Ef, projection pattern of the irradiation light on the fundus Ef is depicted in a photograph image. Further, the image sensor 39 may be sensitive in wavelength bands of illumination light from the illumination system 10. In this case, a photograph image depicts morphology of the fundus Ef and projection pattern of irradiation light.

The irradiation-position specifying part 112 analyzes a photograph image acquired by photographing the fundus Ef on which irradiation light is being irradiated by means of the image sensor 39 to specify irradiation positions of the irradiation light on the fundus Ef. Examples of this processing are described below. Note that presence or absence of illumination by the illumination system 10 is arbitrary at the time of photography of the fundus Ef.

First, the irradiation-position specifying part 112 executes image processing for improving image quality (contrast etc.) of photograph image as necessary.

When illumination by the illumination system 10 is not performed at the time of photography of the fundus Ef, an image region corresponding to a projection pattern of irradiation light (pattern region) is depicted in a photograph image. The irradiation-position specifying part 112 specifies a position of the pattern region in a frame (imaging area) of the photograph image based on pixel values of the photograph image. This position information may be expressed by a two-dimensional coordinate system defined for frames, for example. The controller 101 controls the illumination system 10 (illumination-area changing part) so as to illuminate a site of the fundus Ef corresponding to the specified pattern region. This processing is executed by referring to association information (not illustrated) in which illumination areas by the illumination system 10 and positions in frames are associated with each other, wherein the association information is stored in the storage 120 in advance. From such processing, the illumination system 10 is capable of illuminating a site of the fundus Ef on which irradiation light is being irradiated.

When illumination by the illumination system 10 is performed at the time of photography of the fundus Ef, a projection pattern of irradiation light and morphology of the fundus Ef are depicted in a photograph image. The irradiation-position specifying part 112 specifies a pattern region corresponding to the projection pattern of irradiation light and image region depicting morphology of the fundus Ef (that is, image region corresponding to a site on which illumination light is irradiated: illumination region) based on pixel values of the photograph image. The controller 101 controls the illumination system 10 (illumination-area changing part) so as to make the pattern region and illumination region have predetermined relationship. As a specific example thereof, when the pattern region is included in the illumination region, change of illumination area is not required. On the other hand, at least a part of the pattern region is not included in the illumination region, the controller 101 controls the illumination system 10 (illumination-area changing part) such that illumination region includes the pattern region. From such processing, the illumination system 10 is capable of illuminating a site of the fundus Ef on which irradiation light is being irradiated.

The data processor 110 may specify an image region corresponding to a lesion site of the fundus Ef (lesion region) based on pixel values of a photograph image. This processing is executed based on characteristic morphology or pixel valued (brightness etc.) at the time of photographing a lesion site, for example. The controller 101 may control the illumination system 10 (illumination-area changing part) so as to illuminate this lesion site. The controller 101 may control the galvano scanner 52 based on a positional relationship between the specified lesion region and pattern region corresponding to irradiation light to change position of irradiation light so as to irradiate irradiation light on the lesion region.

Effects of the laser treatment apparatus according to the present modification example are described. The laser treatment apparatus according to the present modification example includes the illumination system 10, photographing system (including the image sensor 39), irradiation system (light source unit 2, laser-irradiation system 50), irradiation-position specifying part 112 and controller 101. The illumination system 10 illuminates the fundus Ef of the eye E. Further, the illumination system 10 includes the illumination-area changing part that changes an illumination area of the fundus Ef. The photographing system photographs the fundus Ef illuminated by the illumination system 10. The irradiation system irradiates aiming light LA of a preset pattern and treatment light LT consisting of laser light of a pattern determined based on the preset pattern of the aiming light LA onto the fundus Ef. The irradiation-position specifying part 112 analyzes a photograph image acquired by photographing the fundus Ef on which the aiming light LA (or treatment light LT) is being irradiated by means of the photographing system to specify irradiation positions of the aiming light LA (or treatment light LT). The controller 101 controls the illumination-area changing part based on specification result from the irradiation-position specifying part to change the illumination area of the fundus Ef by the illumination system 10.

According to such a laser treatment apparatus, illumination area of the fundus Ef can be changed automatically based on photograph image of the fundus Ef on which the aiming light LA (or treatment light LT) is being irradiated. Thereby, it is possible to take the hassle out of adjusting illumination area and facilitate operations of a laser treatment apparatus.

What is claimed is:

1. A laser treatment apparatus comprising:
   an illumination system that illuminates an illumination area of a fundus of an eye, the illumination system including a first light source, a diaphragm, and a first optic that includes the diaphragm, the first optic changing the illumination area, and the diaphragm limiting an amount of light on the illumination area;
   an imaging system configured to observe the fundus illuminated by the illumination system;
   an irradiation system including a second light source and a second optic, which direct light from the irradiation system onto the fundus determined based on a preset pattern and in accordance with an irradiation condition, the light from the irradiation system including aiming light from an aiming light source, which is irradiated based on preset pattern, and treatment light consisting of laser light from a laser, which is irradiated based on the preset pattern, onto the fundus, the aiming light being from an aiming light source and the treatment light being from a laser, which is different from the aiming light source;
   a memory that stores in advance association information, the association information providing a respective illumination area of a plurality of illumination areas for the illumination system in association with each of a plurality of irradiation conditions for the irradiation system, the association information including an arrangement of spots forming the preset pattern; and
   processing circuitry configured to
      set the irradiation condition of the aiming light and/or treatment light from the irradiation system,
      specify, based on the association information stored in the memory, the illumination area of the fundus illuminated by the illumination system, the specified the illumination area being based on the preset pattern of the aiming light and of the treatment light and the set irradiation condition, and
      control the illumination system to change of the illumination area of the fundus to illuminate the arrangement of spots forming the preset pattern, by controlling the diaphragm based on the above association information, wherein
   the irradiation condition includes one or more of (i) an arrangement condition indicating the arrangement of spots forming the preset pattern, (ii) an arrangement size condition indicating size of the preset pattern, (iii) an arrangement orientation condition indicating orientation of the preset pattern, (iv) a spot size condition indicating size of respective spots, and (v) a spot interval condition indicating intervals between spots.

2. The laser treatment apparatus of claim 1, wherein the irradiation-condition setting part includes an operation part for moving irradiation positions of the aiming light on the fundus, and the processing circuitry controls the change of the illumination area according to movement operation of the irradiation positions by means of the operation part.

3. The laser treatment apparatus of claim 1, wherein the diaphragm includes a slit diaphragm comprising a pair of slit blades whose interval is changeable.

4. The laser treatment apparatus of claim 3, comprising a driver that moves the pair of slit blades while keeping the interval of the pair of slit blades constant.

5. The laser treatment apparatus of claim 1, wherein the first optic includes a liquid crystal shutter provided in the illumination system.

6. The laser treatment apparatus of claim 1, wherein the first light source generates light for illuminating the fundus, and the processing circuitry controls the change of the illumination area by changing a light-emitting area in a light-emitting surface of the first light source.

* * * * *